United States Patent
Thakur et al.

(10) Patent No.: US 12,228,573 B2
(45) Date of Patent: Feb. 18, 2025

(54) METHOD OF ISOLATING AND DETECTING EXOSOMAL BIOMARKERS OF GLIOBLASTOMA MALIGNANCY

(71) Applicant: City University of Hong Kong, Kowloon (HK)

(72) Inventors: Abhimanyu Thakur, Kowloon (HK); Wing Kar Li, Kowloon (HK); Youngjin Lee, Kowloon (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 648 days.

(21) Appl. No.: 17/335,605

(22) Filed: Jun. 1, 2021

(65) Prior Publication Data

US 2022/0381782 A1     Dec. 1, 2022

(51) Int. Cl.
*G01N 33/574*     (2006.01)

(52) U.S. Cl.
CPC ............... *G01N 33/57407* (2013.01); *G01N 2333/70585* (2013.01); *G01N 2333/70596* (2013.01)

(58) Field of Classification Search
CPC ... G01N 33/57407; G01N 2333/70585; G01N 2333/70596; G01N 33/54373; G01N 33/54326; Y10T 436/25375

USPC .................. 436/177, 526, 538, 541; 530/413
See application file for complete search history.

(56) References Cited

U.S. PATENT DOCUMENTS

2016/0041175 A1 * 2/2016 Ezrin ................. G01N 33/6875
                                                              435/7.92
2016/0334398 A1 * 11/2016 Weissleder ........... G01N 33/553

OTHER PUBLICATIONS

Deng et al. ("Application of atomic force microscopy in cancer research" J Nanobiotechnol 16:102 (2018)). (Year: 2018).*
Emlet et al. ("Targeting a Glioblastoma Cancer Stem Cell Population Defined by EGF Receptor Variant III" (2014) Cancer Res. 15; 74(4): 1238-1249) (Year: 2014).*

* cited by examiner

*Primary Examiner* — Christopher L Chin
(74) *Attorney, Agent, or Firm* — Conley Rose, P.C.; Michael W. Piper; Andrew M. Metrailer

(57) ABSTRACT

Disclosed herein is a method of diagnosing a malignant glioblastoma. The method can comprise of isolating glioma-derived exosomes from a bodily fluid of the subject, and characterizing the amount of Cluster of Differentiation (CD44) and Cluster of Differentiation 133 (CD133) present in the glioma-derived exosomes. This method allows for the diagnosis of a malignant glioblastoma using CD44 and CD133 levels in EGFRviii specific immunocaptured exosomes from bodily fluids, which has previously not been recognized as providing an indication of a glioblastoma.

1 Claim, 26 Drawing Sheets

Blood Serum Exosomes
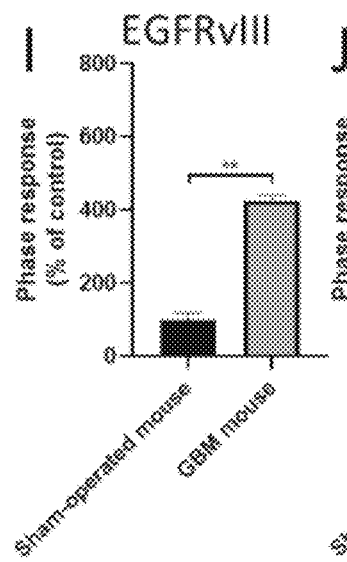
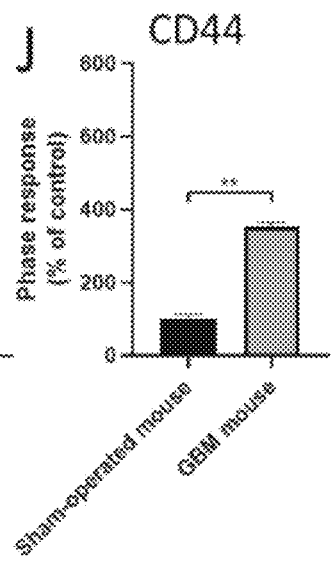
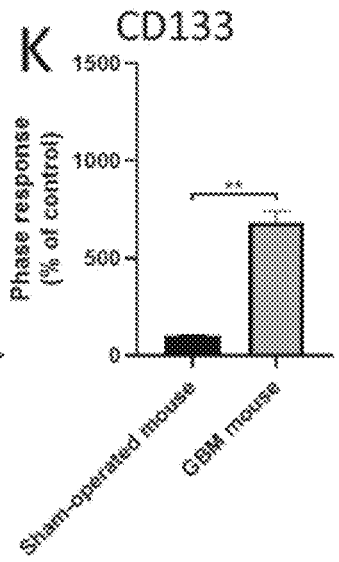
Figure 14                Figure 15                Figure 16
CSF Exosomes
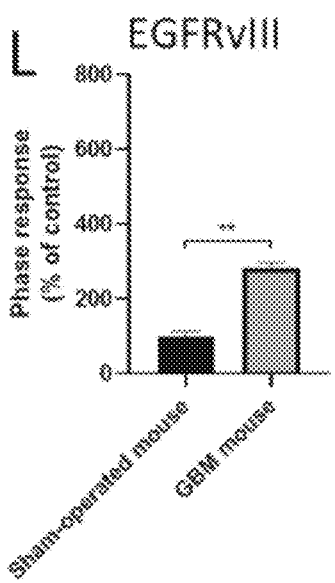
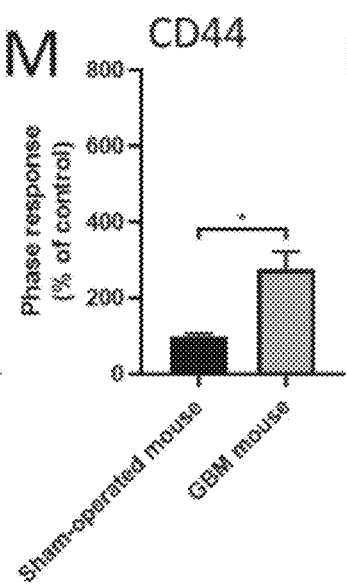
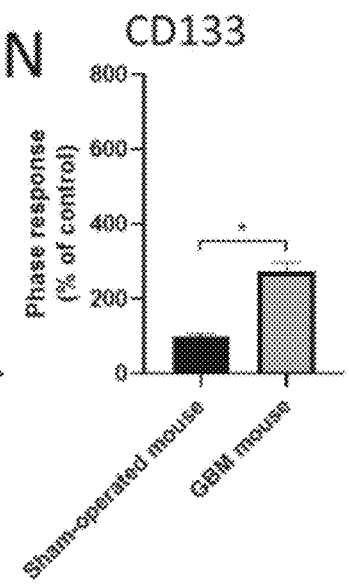
Figure 17                Figure 18                Figure 19

METHOD OF ISOLATING AND DETECTING EXOSOMAL BIOMARKERS OF GLIOBLASTOMA MALIGNANCY

TECHNICAL FIELD

The present disclosure generally relates to detection of biomarkers of glioblastoma. More particularly, the present disclosure relates to use of glioma-derived exosomes for characterization of glioblastoma malignancy in liquid biopsy.

BACKGROUND

The most common fatal tumor in the central nervous system is malignant glioblastoma (GBM), the progression of which is characterized by the increased migration and invasion of GBM cells (GMs) and the enhanced tube formation of endothelial cells.

There are four grades of glioma. Each grade has different types of cells and different types of treatment. A glioblastoma is a grade IV glioma, which is the most aggressive. Hence, not all gliomas are glioblastomas.

Although the efficacy of combined treatments with chemotherapy, radiation, and surgical removal, has been improved, the average survival of patients with malignant GBM is only one and a half years partly because of difficulty in its diagnosis at an early stage and its fast progress with glycolytic reprogramming associated with migration, invasion, and angiogenesis.

As a result of enhanced glycolysis, malignant GMs produce and release a tremendous amount of lactate into the tumor microenvironment. Increased lactate in the tumor microenvironment has been shown to diffuse into tumor-associated fibroblasts and stimulates the synthesis and release of hyaluronic acid, which further enhances the adhesion of GMs and endothelial cells to the reorganized extracellular matrix, leading to tumor growth.

It has also been found that high level of lactate significantly upregulates Clusters of Differentiation 44 (CD44), a cell surface adhesion molecule, in GMs. This promotes the migration of GMs via the interaction with its ligand, hyaluronic acid, in reorganized extracellular matrix. That is, when GMs enhance the expression of Epidermal Growth Factor Receptor Variant-Ill (EGFRviii), a tumor-specific protein, CD44 is significantly upregulated and distributed in the membrane of filopodia of GMs, which increases their migration and invasion. It has been well demonstrated that level of hyaluronic acid, CD44, and their interactions are positively correlated with tumor severity. Conversely, inhibitors for hyaluronic acid-CD44 interactions have shown anticancer effects, further indicating that their interactions are essential in tumor progression.

Besides CD44, a prominent prognostic cancer biomarker, CD133, has been also proven to be upregulated in lactate-enriched hypoxic tumors. Therefore, tissue levels of hyaluronic acid, CD44 and CD133 in patients can be precise biomarkers to track tumor malignancy. However, analyzing tissues for hyaluronic acid, CD44, and CD133 in tissues requires painful biopsy.

Liquid biopsy has been proposed which harvests biomarkers from bodily fluids such as blood or cerebrospinal fluid. However, it has not been shown that GBM biomarkers can be found in fluids and therefore useable for liquid biopsy of GBM. Furthermore, as bodily fluids travel through the body, it is so far impossible to determine if a detected biomarker, such as CD44, is produced by GMs.

Accordingly, it is desirable to propose a non-invasive method for detecting biomarkers to trace the malignancy of GBM from bodily fluids alone.

SUMMARY OF THE INVENTION

In a first aspect, the invention proposes use of blood or cerebrospinal fluid exosomal CD44 as biomarker for GBM. Alternatively, the invention proposes use of blood or cerebrospinal fluid exosomal CD133 as biomarker for GBM.

Before the present invention, it was not possible to use GMs-specific exosomal CD44 isolated from blood or cerebrospinal fluid as a biomarker for GBM, as it was not known to be indicative of GBM. Similarly, it was not possible to use GMs-specific exosomal CD133 isolated from blood or cerebrospinal fluid as a biomarker for GBM until the present invention. The novel use as proposed by the invention therefore provides the possibility of liquid biopsy on samples of bodily fluids.

Typically, the exosomes that comprises EGFRviii, are found to be originating from GMs. This allows CD44- or CD133-containing exosomes originating from GBM to be separated from exosomes in the same bodily fluids that originated from other sources in the body, by using antibodies that are specific to EGFRviii and then characterized.

Accordingly, the invention provides the advantageous possibility of using exosomes released by GMs and which have entered the bloodstream across the blood brain barrier, or which has entered the cerebrospinal fluid across the blood-cerebrospinal fluid-barrier to be harvested for diagnostic use.

In a second aspect, the invention proposes a liquid biopsy method, comprising the steps of: providing a sample comprising blood or cerebrospinal fluid; separating exosomes comprising the EGFRviii in the blood or cerebrospinal fluid; affixing the separated exosomes on a substrate; and characterizing the amount of Cluster of Differentiation (CD44) and/or Cluster of Differentiation 133 (CD133) present in the exosomes.

Preferably, the substrate comprises a layer of titanium nitride (TiN), and a layer of biotinylated CD63 antibody on the layer TiN; such that the step of affixing the separated exosomes on a substrate comprises the further steps of: affixing the separated exosomes to the substrate by the attraction between CD63 on the separated exosomes and the biotinylated CD63 antibody on the titanium nitride layer.

TiN is one of the promising plasmonic materials. Therefore, this provides the possibility of a using Titanium Nitride-Nanoholes-Localized Surface Plasmon Resonance (TiN-NH-LSPR) biosensor to detect tiny amount of exosomal proteins in blood and cerebrospinal fluid, allowing unprecedented sensitivity to the biomarkers of CD44 or CD133.

Optionally, the step of separating exosomes comprising the EGFRviii in the blood or cerebrospinal fluid comprises the further steps of providing magnetic beads affixed with anti-EGFRviii antibody; mixing the magnetic beads into the blood or cerebrospinal fluid such that the exosomes comprising EGFRviii are attached to the anti-EGFRviii on the magnetic beads; using a magnet to move the magnetic beads affixed with anti-EGFRviii antibody away from the blood or cerebrospinal fluid; using a release buffer solution to break the attachment between the exosomes and the anti-EGFRviii on the magnetic beads; using a magnet to remove the magnetic beads from the exosomes.

In a further aspect, the invention proposes a magnetic bead having specificity for CD44, CD133 or EGFRviii associated with GMs-derived exosomes.

BRIEF DESCRIPTION OF THE DRAWINGS

It will be convenient to further describe the present invention with respect to the accompanying drawings that illustrate possible arrangements of the invention, in which like integers refer to like parts. Other embodiments of the invention are possible, and consequently the particularity of the accompanying drawings is not to be understood as superseding the generality of the preceding description of the invention.

Figure 13A:
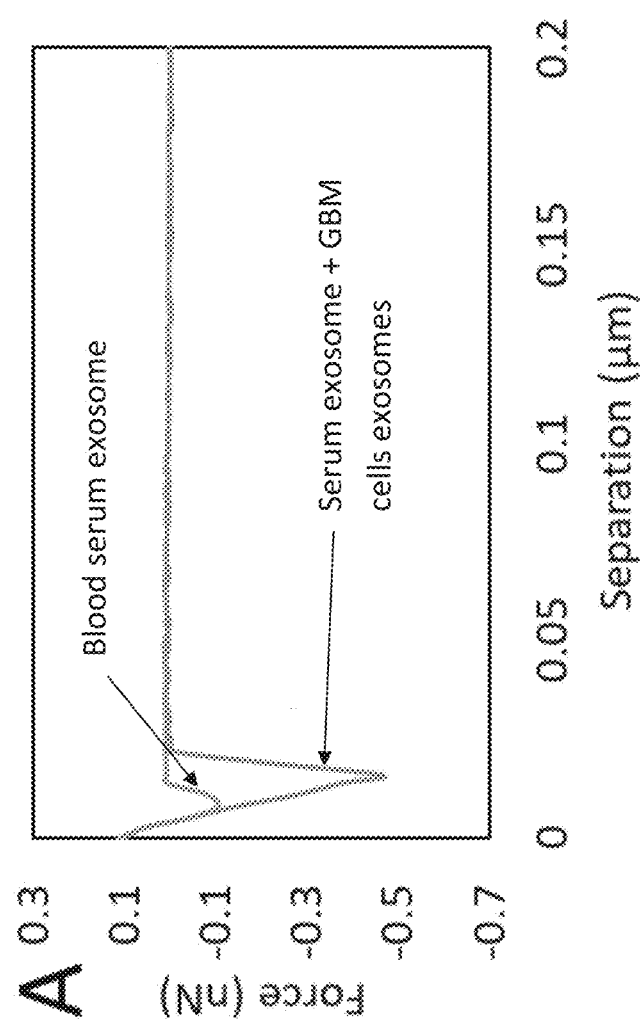
Figure 13B:
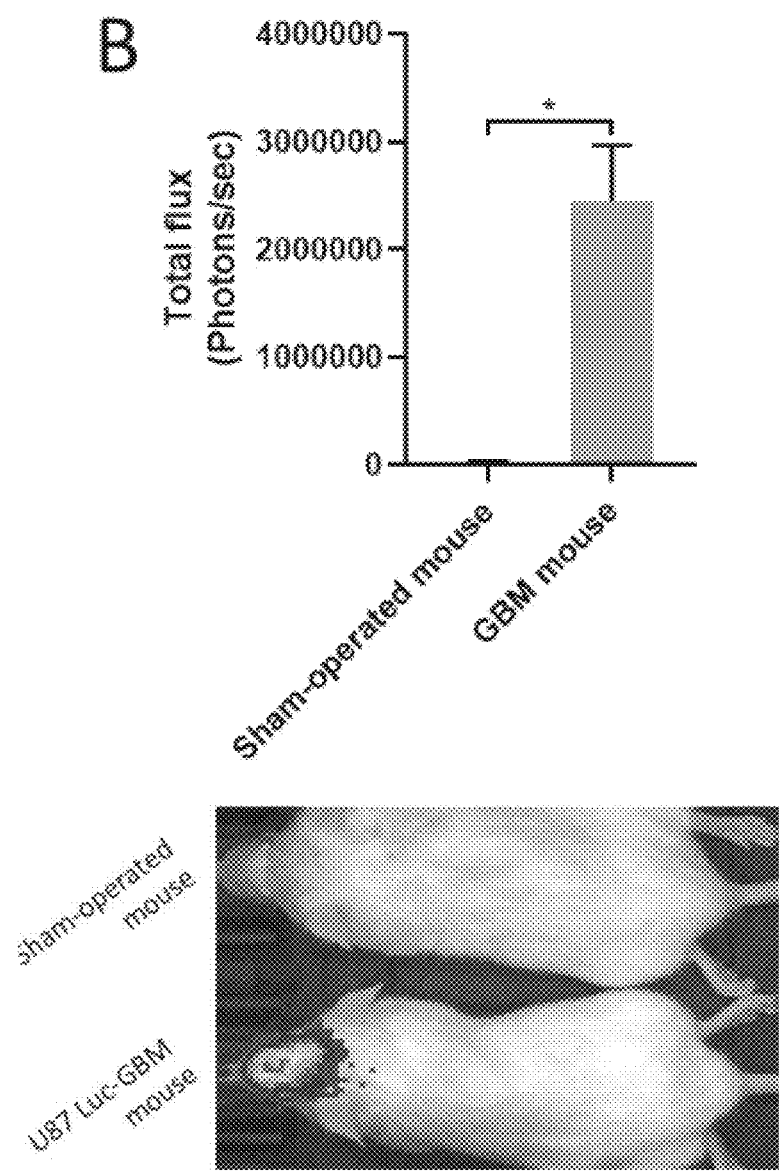
Figure 13C:
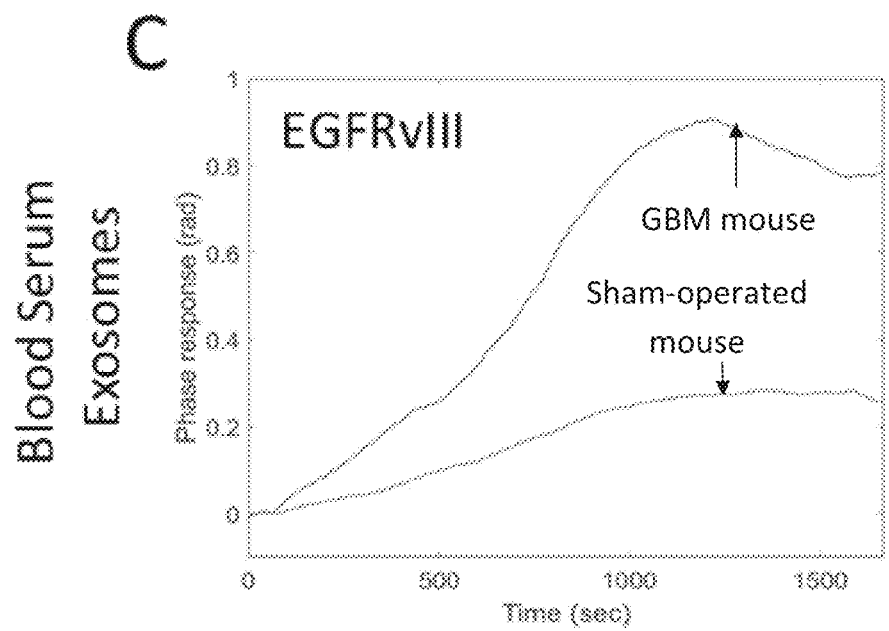
Figure 13D:
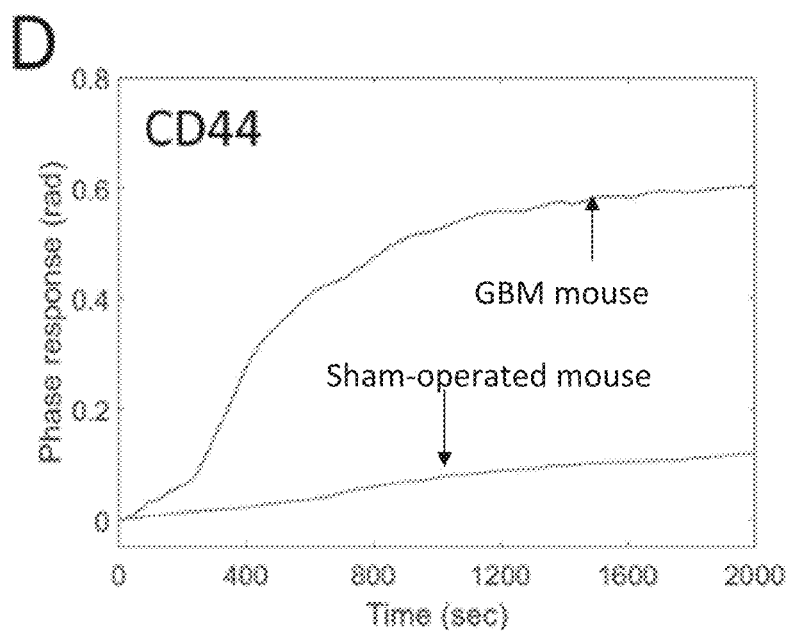
Figure 13E:
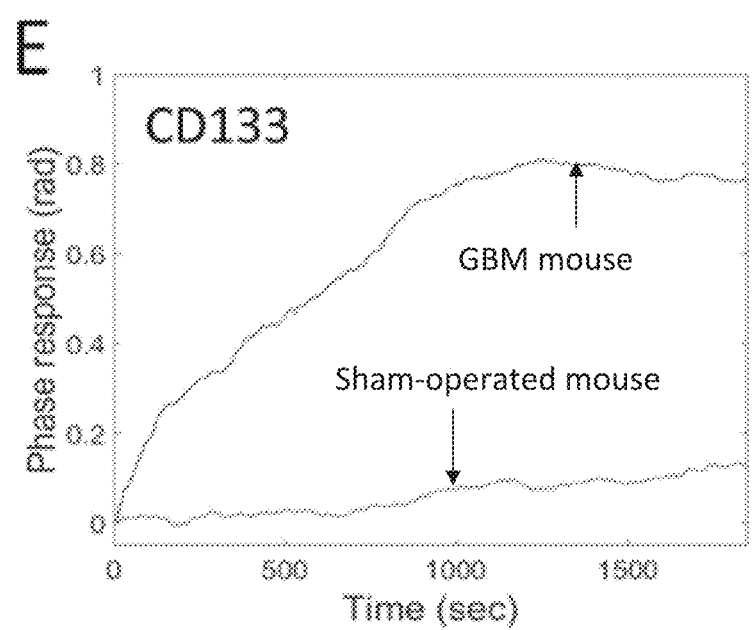
Figure 13F:
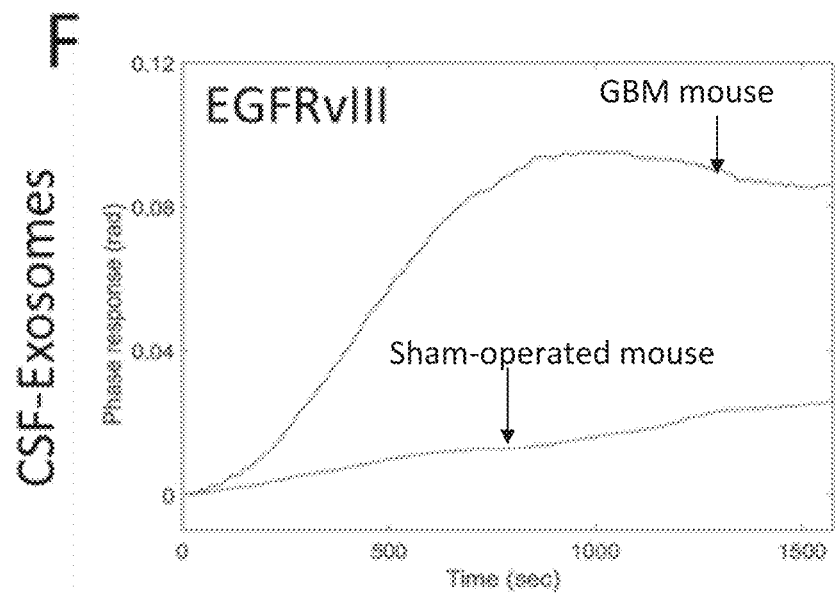
Figure 13G:
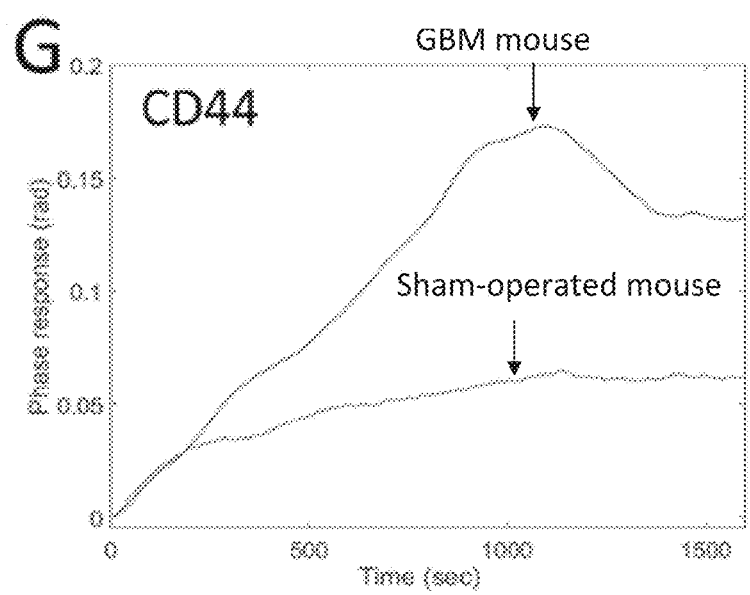
Figure 13H:
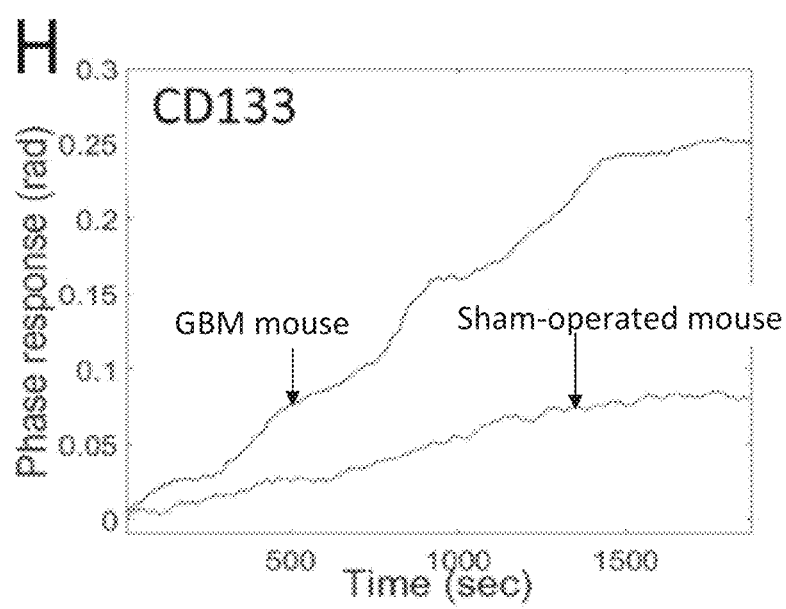
Figure 20:
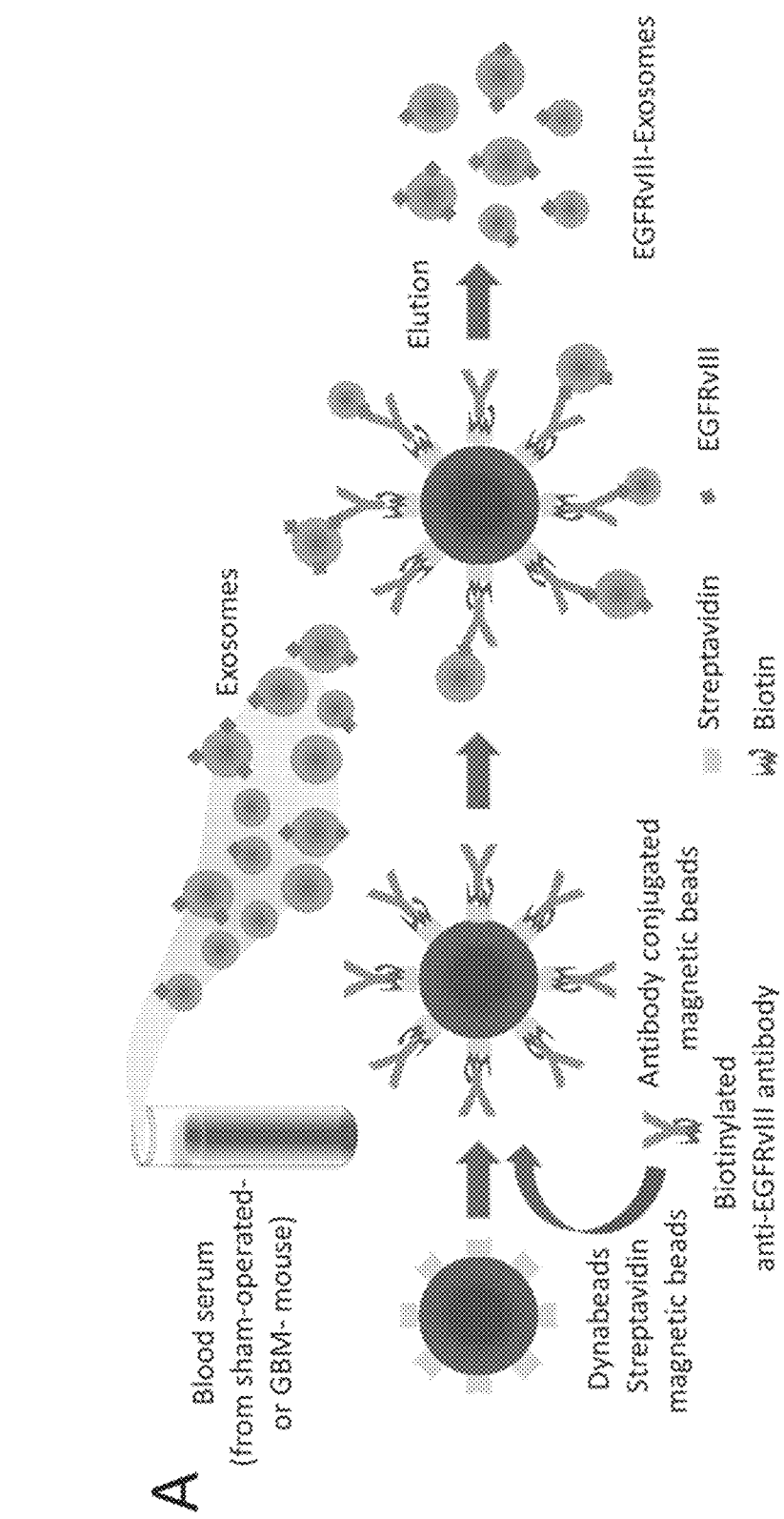
Figure 21:
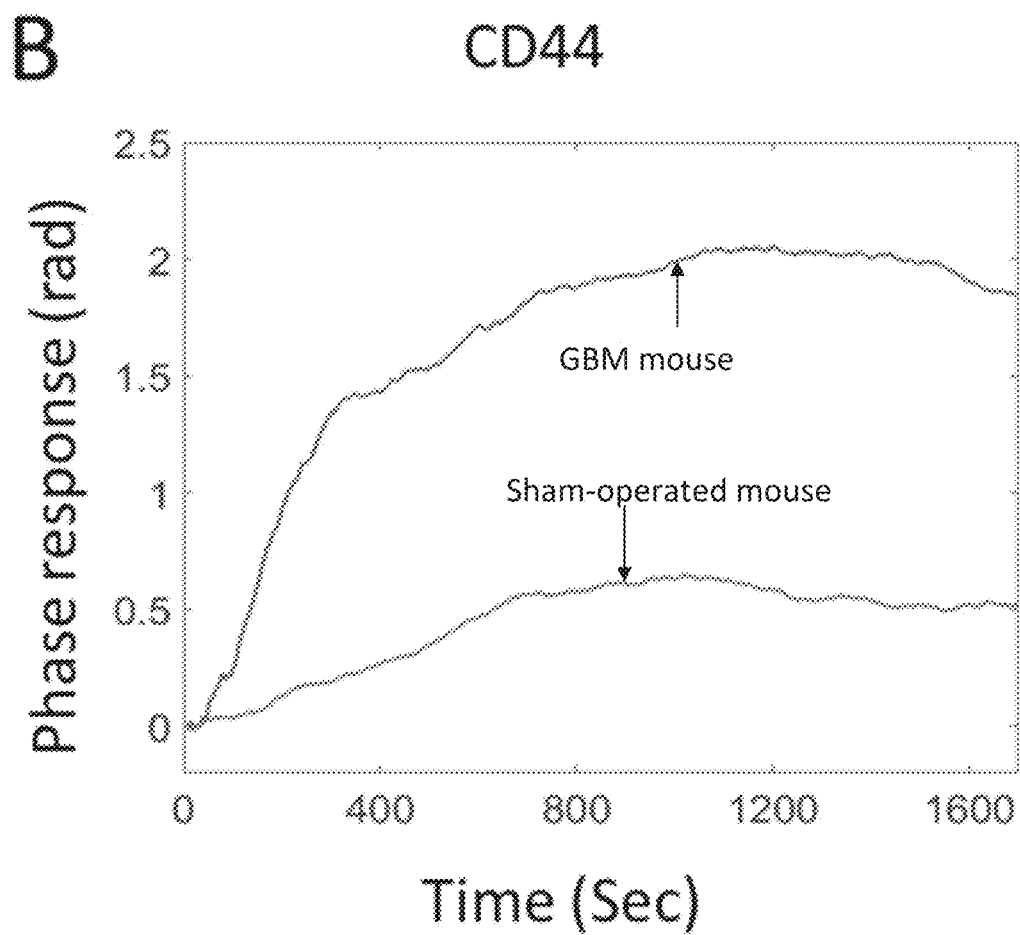
Figure 22:
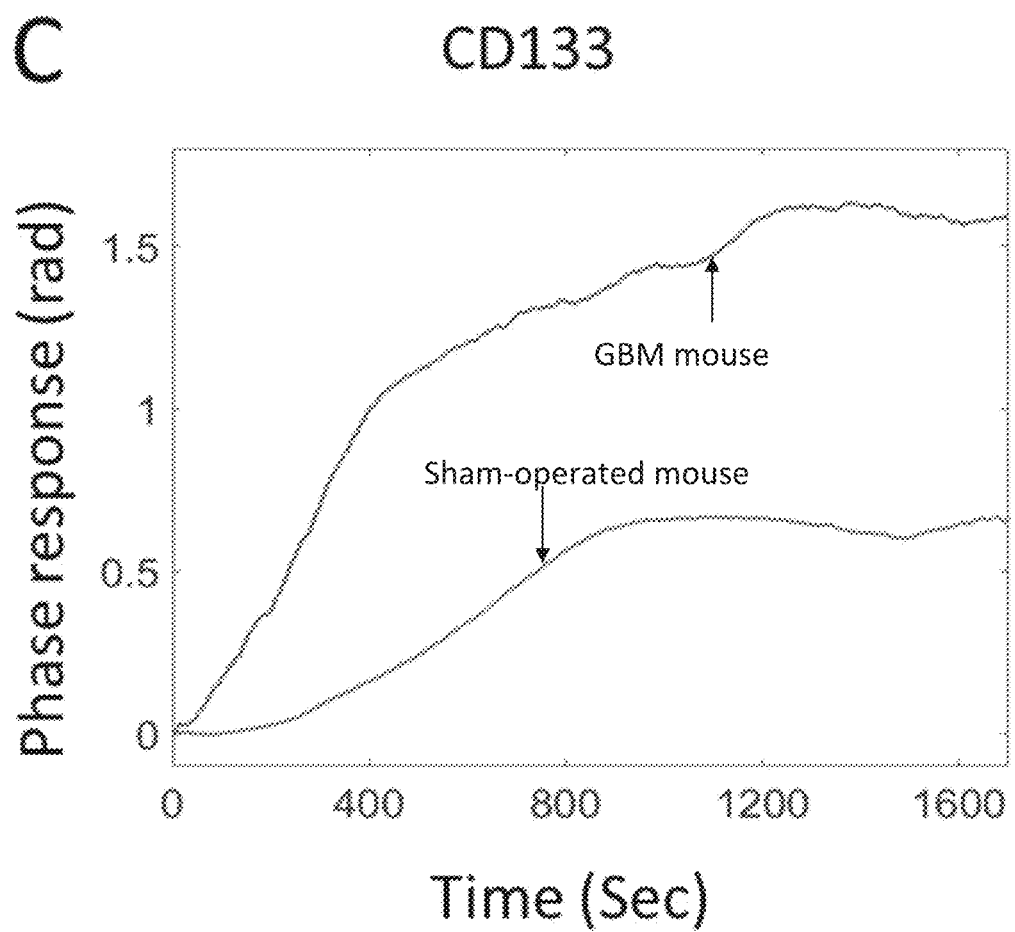
Figure 23:
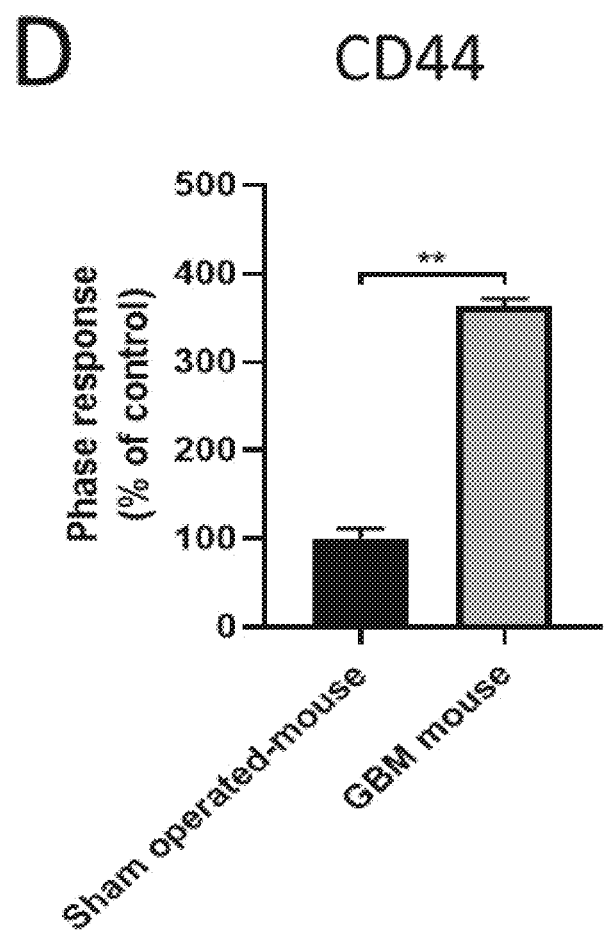
Figure 24:
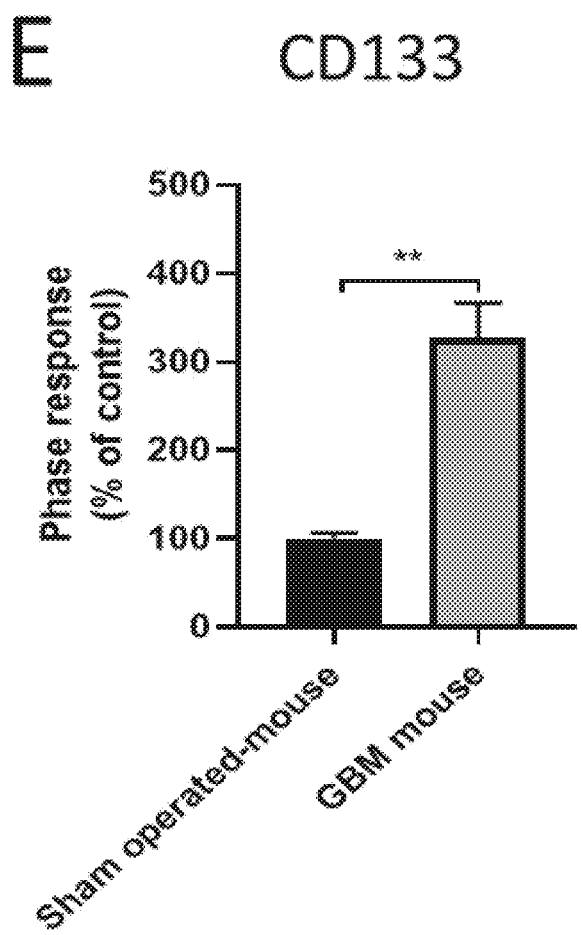
Figure 25:
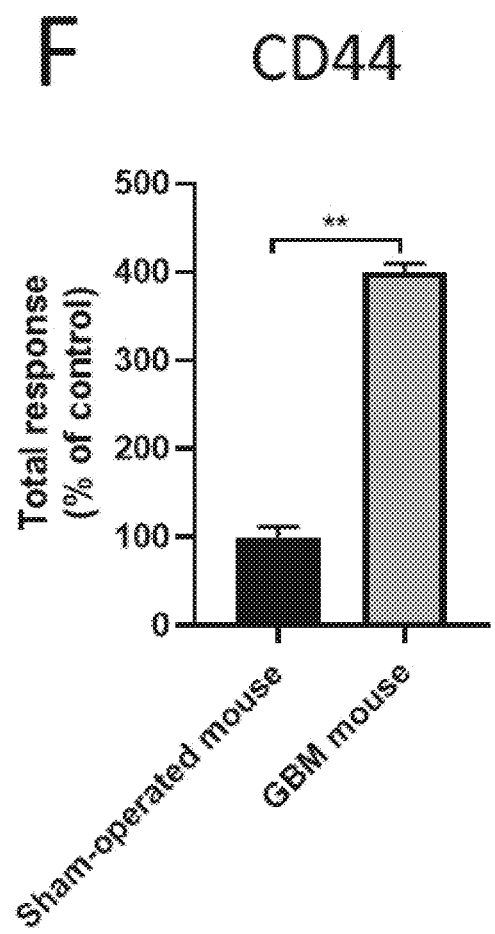
Figure 26:
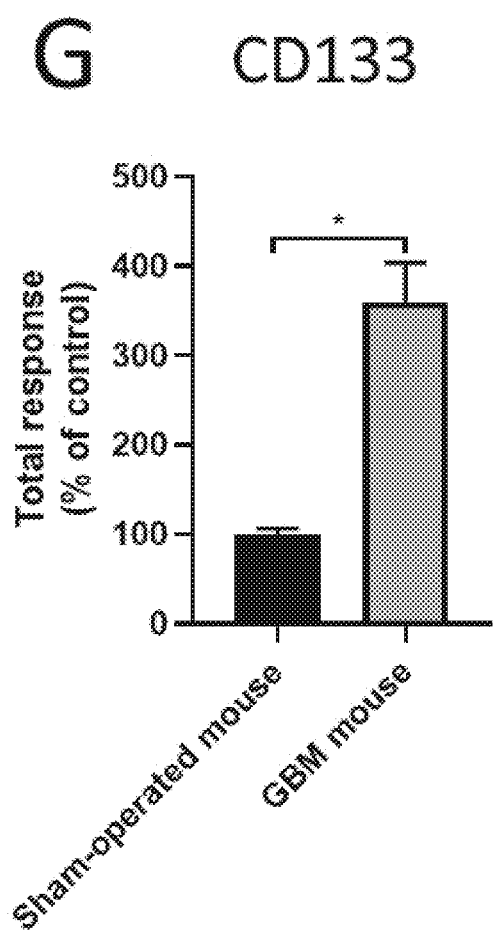
Figure 27:
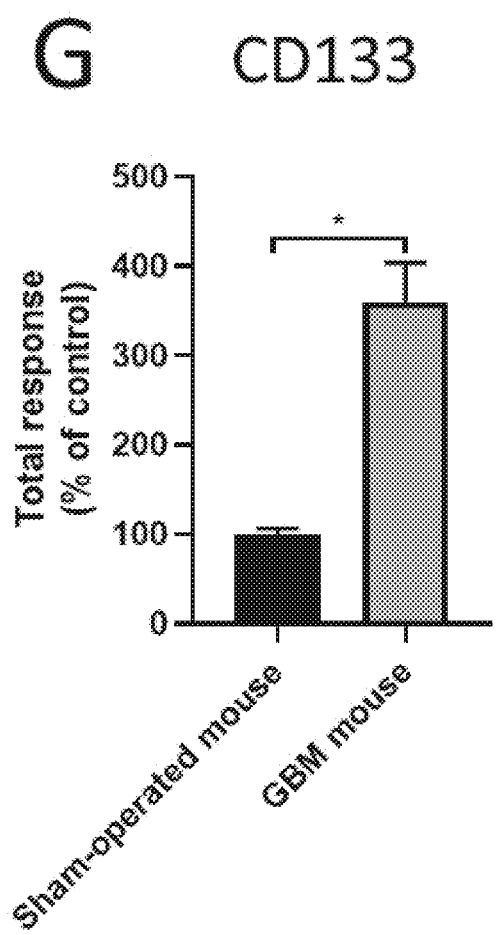

The following figures are experimental results supporting the feasibility of the embodiments described in FIG. 1 to FIG. 12;

FIG. 13A are Atomic Force Microscopy force curves, showing the stronger interaction force between CD44 AB on the tip and CD44 in EGFRviii AB-captured GMs-derived exosomes from the mixture with the blood serum and GMs-derived exosomes as compared to that of control blood serum-derived exosomes (A) and the corresponding bar graph summarizing their relative strength (B);

FIG. 13B shows representative bioluminescence (BLI) images of the intracranial GBM of the mouse implanted with U87 Luc-GMs;

FIG. 13C, FIG. 13D, FIG. 13E show the response of EGFRviii, CD44 and CD133 taken from blood serum exosomes;

FIG. 13F, FIG. 13G, FIG. 13H shows the response of EGFRviii, CD44 and CD133 taken from cerebrospinal fluid exosomes;

FIG. 14, FIG. 15, FIG. 16 all show the cases in which each biomarker is expressed in blood, between the sham control and the GBM mice;

FIG. 17, FIG. 18, FIG. 19 all show the cases in which each biomarker is expressed in cerebrospinal fluid, between the sham control and the GBM FIG. 20 shows how GMs-derived exosomes in the blood serum and the cerebrospinal fluid were isolated by magnetic dynabeads immunocapture using EGFRviii AB;

FIG. 21 shows that the phase response of CD44 is greater in the GMs;

FIG. 22 shows the CD133 response is greater in the GMs;

FIG. 23 shows the CD44 response is greater in phase response for the GBM mouse than that of the sham operated mouse;

FIG. 24 shows the CD133 response is greater in phase response for the GBM mouse than that of the sham operated mouse;

FIG. 25 shows the CD44 response is greater in total response for the GBM mouse than that of the sham operated mouse;

FIG. 26 shows the CD133 response is greater in total response for the GBM mouse than that of the sham operated mouse.

DESCRIPTION OF EMBODIMENTS

Figure 1:
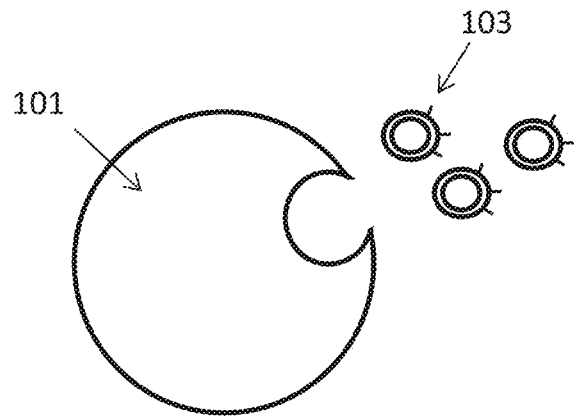
FIG. 1 illustrates a cancer cell releasing exosomes.

FIG. 1 is a schematic illustration of a GBM cancer cell 101. The GBM cancer cell 101 is shown releasing exosomes 103. Exosomes 103 are membrane-bound extracellular vesicles (EVs) that are produced in the endosomal compartment of eukaryotic cells. Generally, exosomes 103 are about 30 nm to 150 nm in diameter, and can be found in most bodily fluids, including saliva, blood, cerebrospinal fluid, urine etc.

Figure 2:
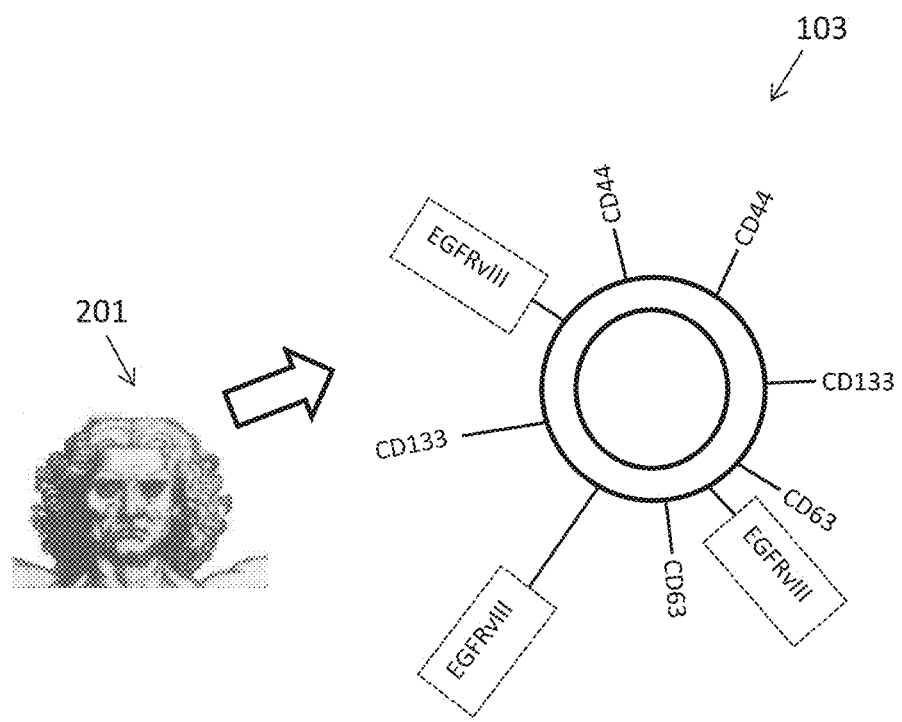
FIG. 2 schematically illustrates an exosome such as that shown in FIG. 1, released in bodily fluids (such as blood and CSF) of a human having GBM.

FIG. 2 illustrates schematically a person 201 having GBM (invisible in illustration). The tumour cells of the GBM release exosomes 103 that can cross the blood brain barrier and be detected in both blood and cerebrospinal fluid. Typically, exosomes 103 of GBM contains a high level, or upregulated biomarkers. Among these are CD44 (Cluster of differentiation 44), CD133 (Cluster of differentiation 133), CD63 (Cluster of differentiation 63) and (Epidermal Growth Factor Receptor Variant-III) EGFRviii.

A particular Cluster of CD44 is associated with the pathologic activities of cancer cells. Hence, CD44 is useable as a biomarker for cancer. CD44 is also a receptor for hyaluronic acid.

Besides CD44, Cluster of differentiation 133 (CD133) is also a commonly used marker for isolation of cancer stem cell (CSC) population from gliomas and carcinomas.

Cluster of differentiation 63 (CD63) antigen is a human protein that mainly associated with membranes of intracellular vesicles.

Epidermal Growth Factor Receptor Variant III (EGFRviii) is a growth factor that is commonly found in GBM. EGFRviii is specifically expressed in cancer cells, promoting their malignant aggressiveness as presented by enhanced invasion and angiogenesis. Therefore, an increased expression of EGFRviii is typically associated with the poor prognosis of GBM.

These biomarkers known to the skilled man and further elaboration is not necessary. It suffices herein to state that all these markers are found on the surfaces of exosomes released by GMs. That is, in a person with GBM, a large amount of lactate is released in the tumour environment (tumor microenvironment), this leads to an upregulation, or an increase, of CD44, CD133 and EGFRviii. Hence, it is possible to detect CD44, CD133 and EGFRviii in blood or cerebrospinal fluid for tracking the progress of GBM.

Figure 3:
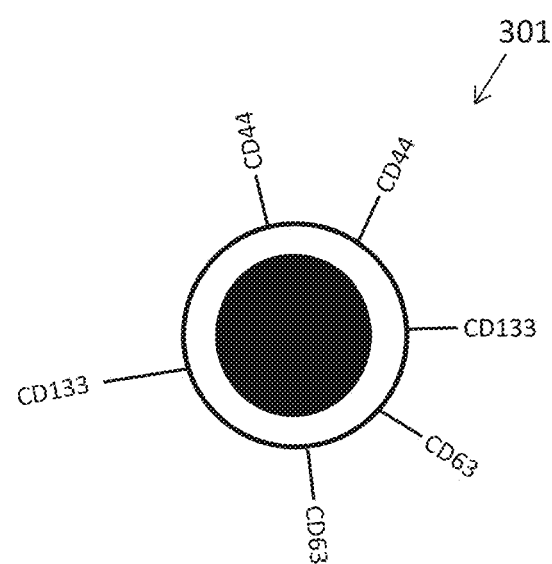
FIG. 3 illustrates an exosome that is not produced by GBM.

FIG. 3 illustrates an exosome 301 that is produced by other cells of the body instead of GMs, i.e. a non-GBM exosome 301. GBM exosomes 103 has the protein EGFRviii on the exosome surface. Non-GMs tend to produce exosomes 301 that do not have EGFRviii on the exosome surface.

Figure 4:
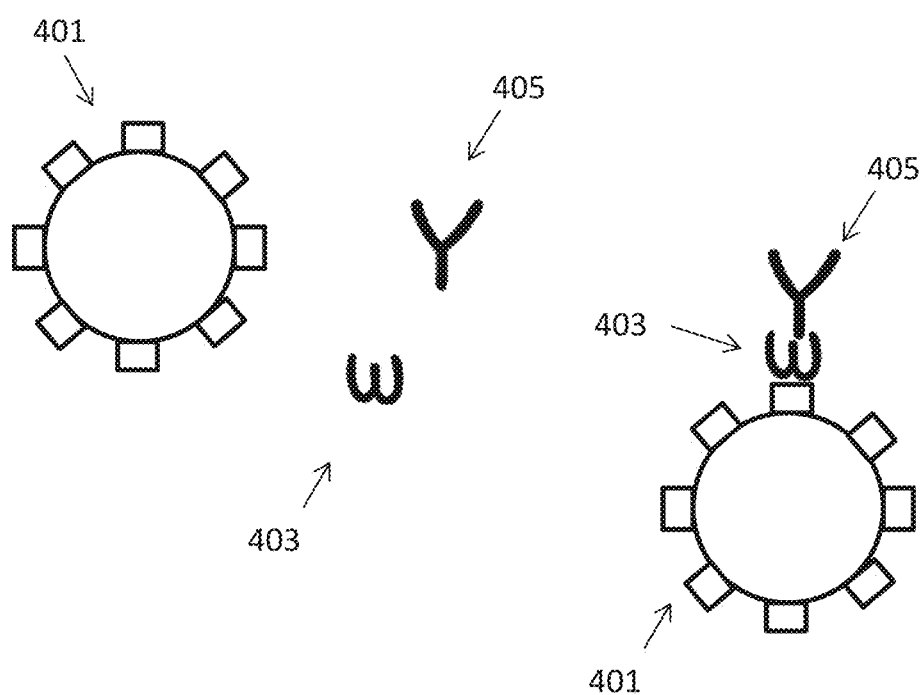
FIG. 4 shows a magnetic bead that is affixed with an antigen.

FIG. 4 shows how a Dynabeads™ Streptavidin magnetic bead 401 is used to capture cancer-cell-produced exosomes. Dynabeads™ Streptavidin magnetic beads 401 are uniform and superparamagnetic beads 401 are 2.8 µm in diameter, with a monolayer of recombinant streptavidin covalently coupled to the surface The monolayer of streptavidin is for binding of biotinylated ligands/targets.

Streptavidin is not the only protein capable of binding to biotin with high affinity. Avidin is the other most notable biotin-binding protein. Hence, the embodiment is not limited to just Dynabeads™ Streptavidin magnetic bead 401.

Figure 5:
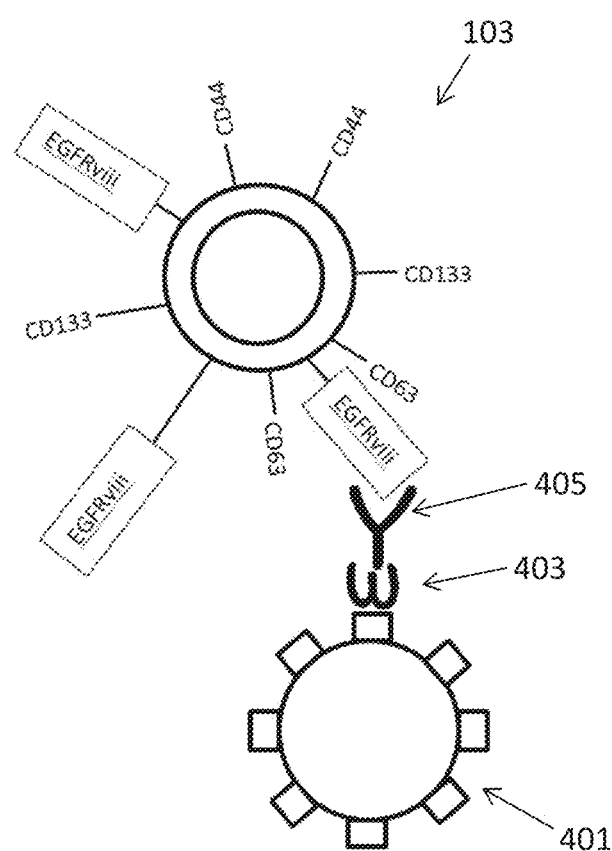
FIG. 5 shows how the magnetic bead of FIG. 4 is used to bind selectively to the exosome of FIG. 1.

In FIG. 4, a Dynabeads™ Streptavidin magnetic bead 401 is mounted to a biotin 403, which is in turn bound to an anti-EGFRviii antibody 405. FIG. 5 shows how an assembled magnetic bead 401 bound to anti-EGFRviii antibody is quite capable of binding to free floating exosomes in bodily fluid samples such as blood or cerebrospinal fluid.

FIG. 5 shows a GBM exosomes having the EGFRviii protein on the exosome surface is captured by the anti-EGFRviii antibody 405 on the Dynabeads™ Streptavidin magnetic bead 401.

Figure 6:
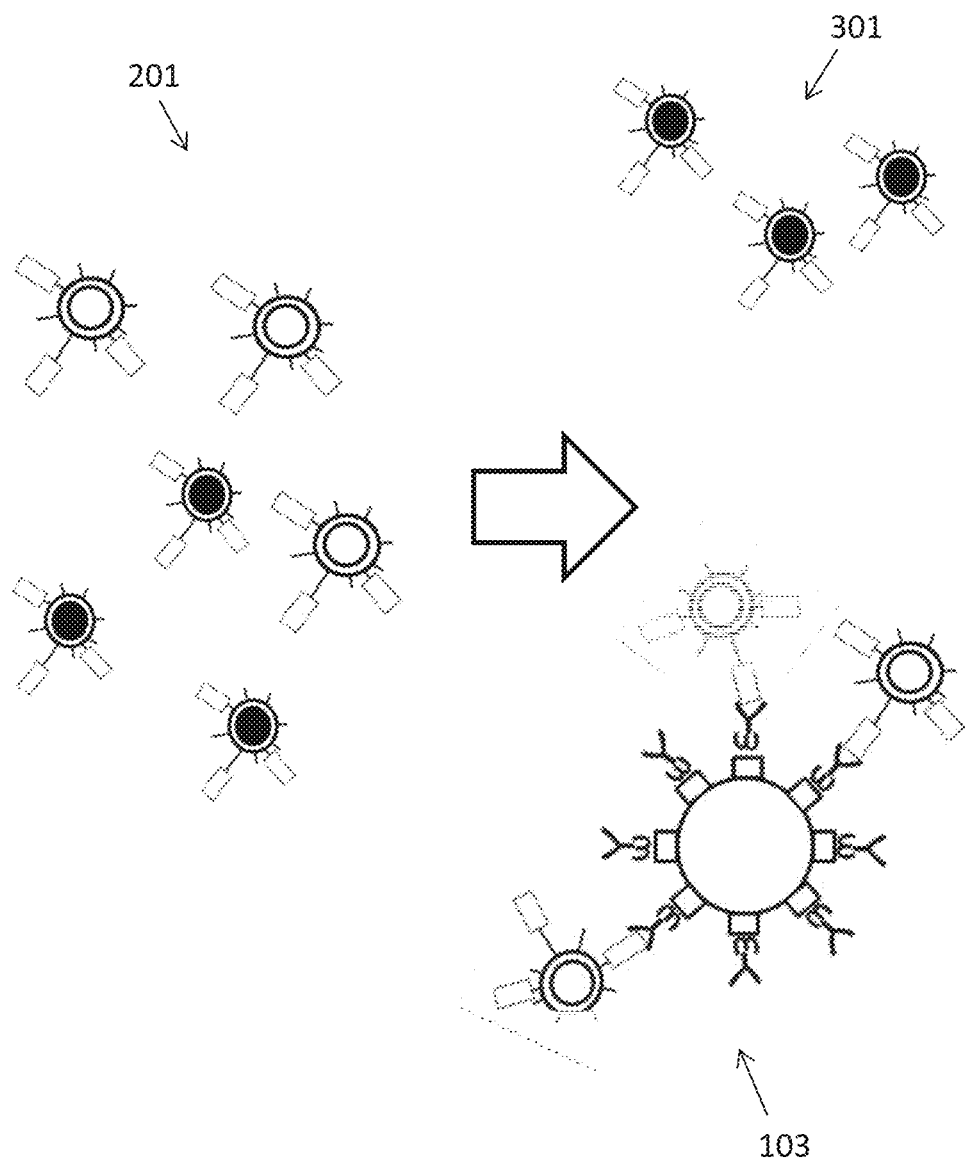
FIG. 6 expands on FIG. 5 to show how exosomes of FIG. 1 are harvested from a mixture of exosomes of both FIG. 1 and FIG. 3.

FIG. 6 shows how a mixture of GBM exosomes 103 and non-GBM exosomes 301 are separated by the Dynabeads™ Streptavidin magnetic bead 401. The magnetic beads 401 respond to a magnetic field, allowing bound GBM exosomes 103 to be rapidly and efficiently collected on the magnet and separated from the remaining exosomes in the blood or cerebrospinal fluid sample. Unbound material remains in the supernatant and is simply removed by aspiration. The bead-bound GBM exosomes 103 is released from the surface of the magnetic bead 401 for binding to the titanium nitride substrate.

Titanium nitride (TiN) has been found to be a promising iasmonic material for the detection of biomolecules such as exosomes, due to its characteristics of low resistivity, corrosion resistance, tunable optical absorption, high microhardness, chemical, and thermal stability.

For example, a sensing chip coated with titanium nitride nanofilm facilitates the tuning of plasmonic effect in the mid-visible spectrum and a single coating of titanium nitride on the chip provides lower confinement loss. Additionally, surface electromagnetic wave can be further localized and amplified by introducing nanostructures such as nanoholes to titanium nitride nanofilm, generating more sensitive Localized Surface Plasmon Resonance response towards biomolecules. Therefore, it has been in demand to address whether the TiN-NH-LSPR biosensor with strong localization of surface plasmon polaritons can produce enough sensitivity in Localized Surface Plasmon Resonance response to detect tiny amount of exosomal proteins in blood and cerebrospinal fluid.

Figure 7:
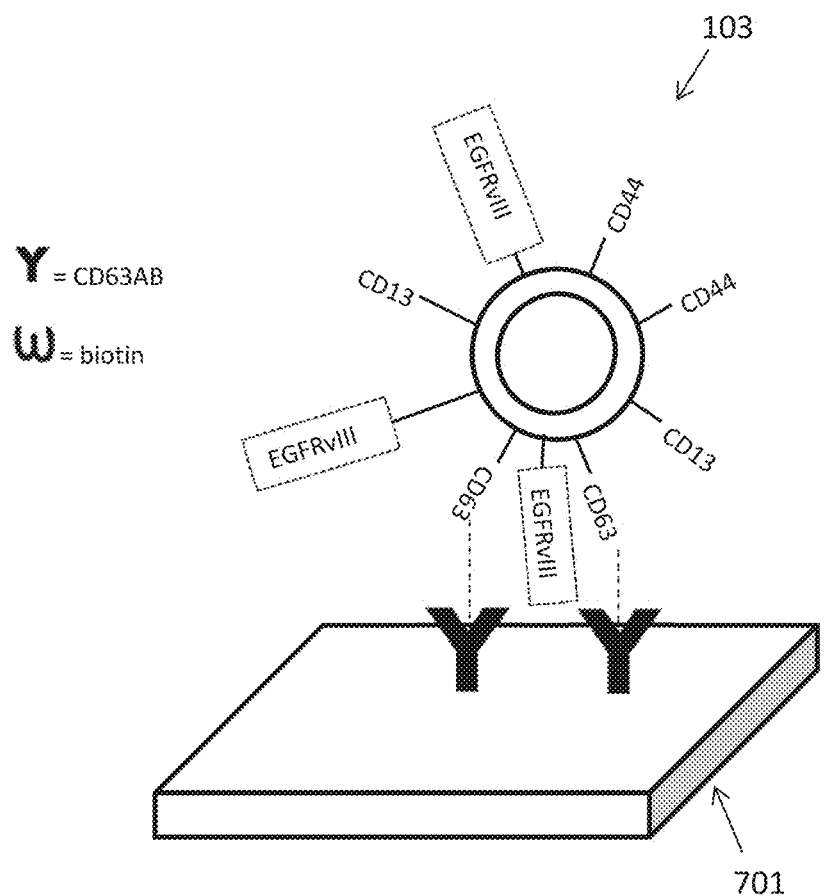
FIG. 7 shows how the exosomes harvested in the process of FIG. 6 is affixed to a titanium nitride surface for analysis by plasmonic biosensors.

FIG. 7 shows how GBM exosomes may be immobilized on a titanium nitride substrate 701. Generally, a substrate support is provided. On the substrate 701 is provided with the layer of titanium nitride. On the titanium nitride is affixed with a layer of CD63 antibody using biotin as the adherent, biotinylated CD63AB. CD63 is commonly found in all human cells and exosomes. Hence, when GBM exosomes 103 harvested using magnetic beads 401 is passed over the CD63AB, the GBM exosomes 103 are affixed to the titanium nitride substrate by CD63 on the surface of the GBM exosome 103. The titanium nitride substrate 701 can be subject to Titanium Nitride-Nanoholes-Localized Surface Plasmon Resonance (TiN-NH-LSPR) spectroscopy.

Besides using TiN-NH-LSPR, or other forms of Localized Surface Plasmon Resonance, Atomic Force Microscopy can also be used to detecting and characterise the presence of CD44 and/or CD133.

As the skilled reader would know, Atomic Force Microscopy is a very sensitive instrument which comprises a very tiny cantilever 801 that is dragged over very small surfaces such as that of a cell or even an exosome. The surface can be mapped and profiled, and the chemical affinity of the surface can be detected as the cantilever 801 runs across the surface.

Figure 8:
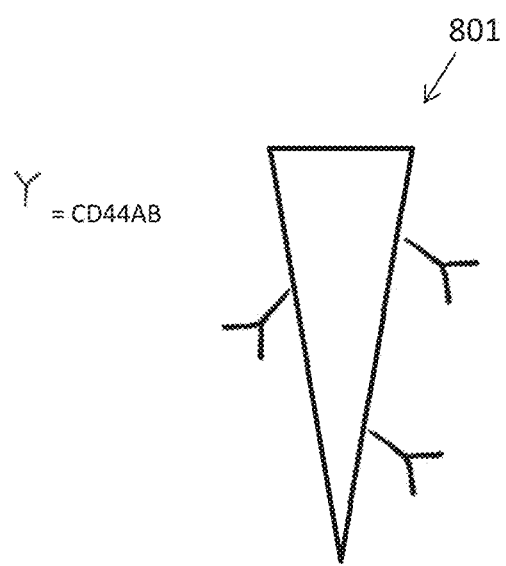
FIG. 8 illustrates the cantilever of an atomic force microscope.
Figure 9:
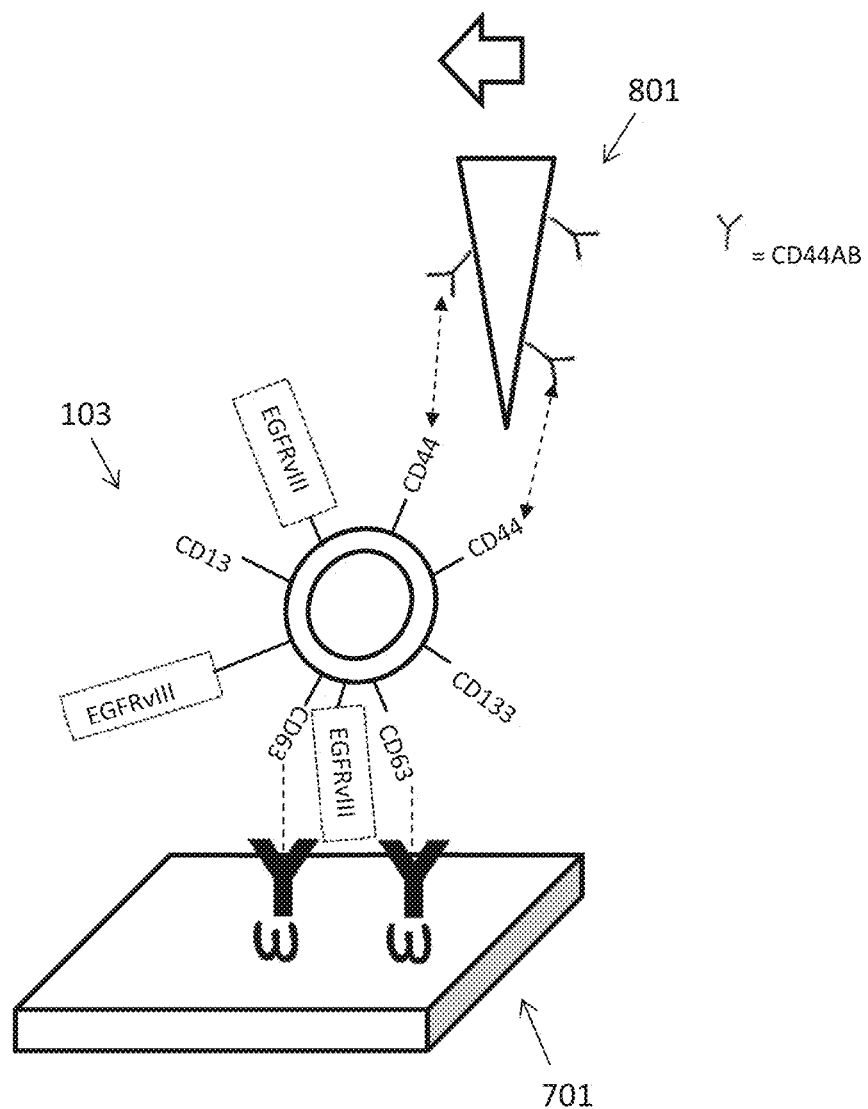
FIG. 9 illustrates the movement of the cantilever of FIG. 8.
Figure 10:
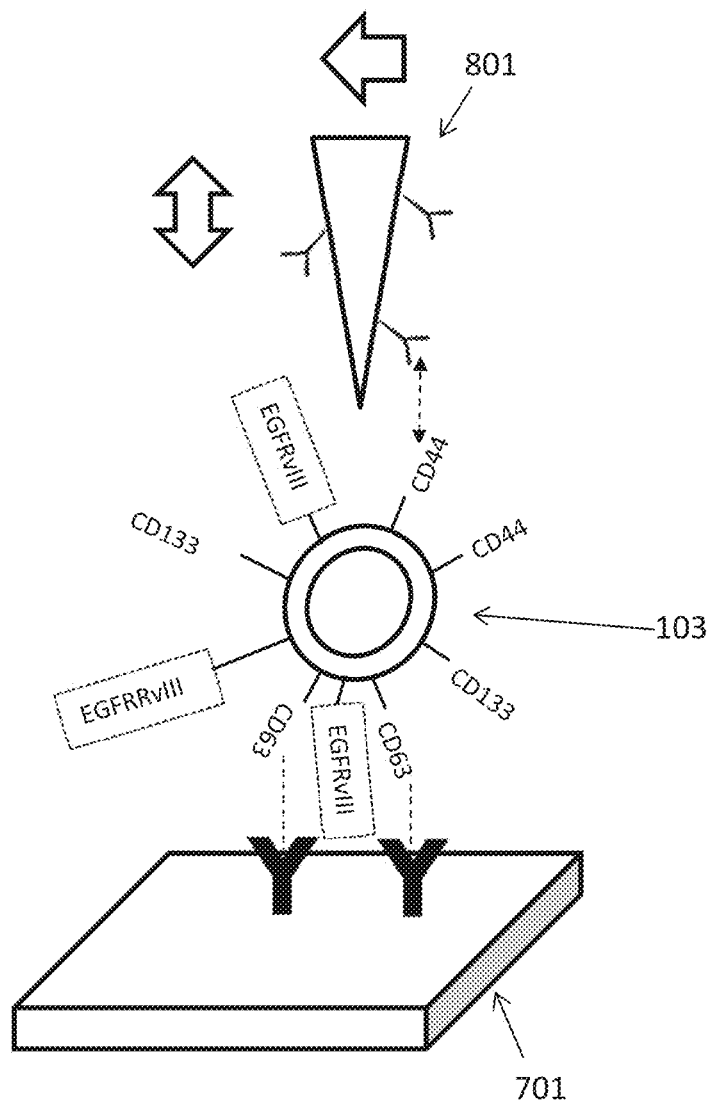
FIG. 10 further illustrates the movement of the cantilever of FIG. 8.
Figure 11:
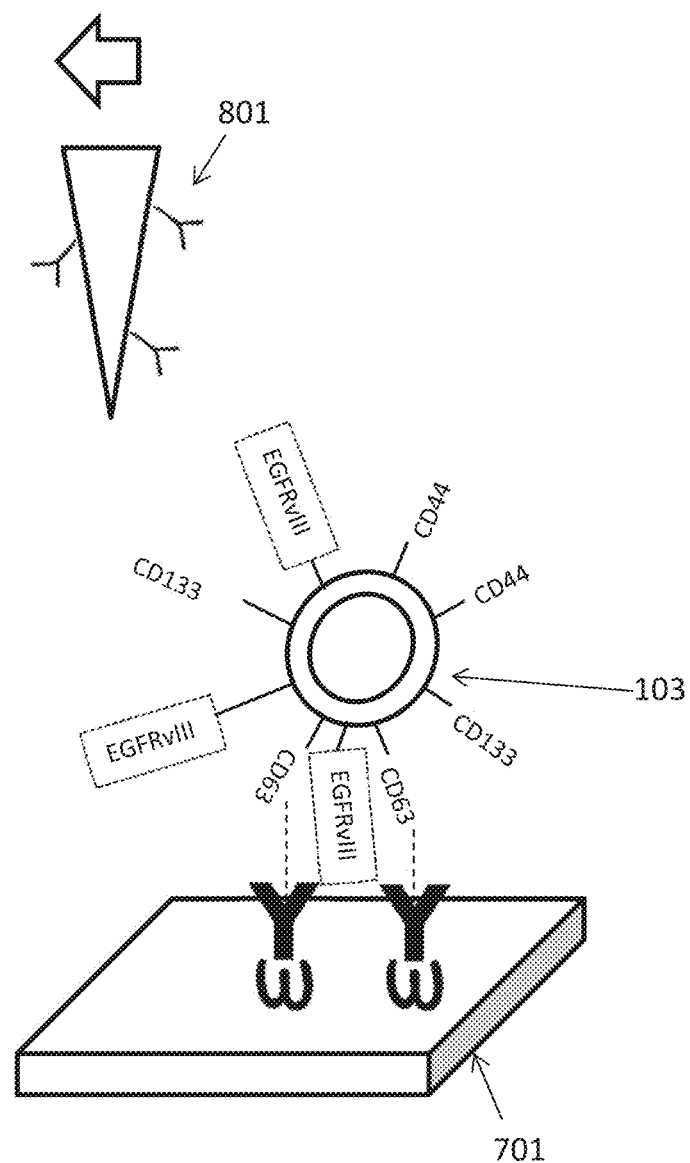
FIG. 11 yet further illustrates the movement of the cantilever of FIG. 8.

FIG. 8 illustrates the cantilever 801 of an atomic force microscope. The surface of the cantilever 801 is affixed with the ligand for CD44, i.e. CD44AB. During Atomic Force Microscopy, the cantilever 801 is moved across the surface of the titanium nitride substrate 701 to which the exosomes are bound, in the direction shown by the white arrow. The CD44AB is attracted to the CD44 on the surface of the exosomes. For the cantilever 801 to be moved past a CD44, the force moving the cantilever 801 must overcome the attraction between the CD44AB and the CD44. The more CD44 on the surface of the exosomes, the more force is required for moving the cantilever 801 over the surface of the exosomes. Accordingly, FIG. 9 shows schematically attraction forces between CD44AB on the cantilever 801 and CD44 on the surface of the exosomes. FIG. 10 shows schematically some of the attraction forces between CD44 and CD44AB broken as the cantilever 801 moves on in the direction of the white arrow. FIG. 11 shows all the forces between CD44AB on the cantilever 801 and the CD44 on the exosome broken as the cantilever 801 moved past the exosome.

Preferably, as illustrated by the double-headed arrow in FIG. 10, the cantilever 801 applies a tapping action on the exosomes. This further tests the attraction forces between the CD44 on the exosome and CD44AB on the cantilever 801 to characterise both the presence and amount of CD44.

Figure 12:
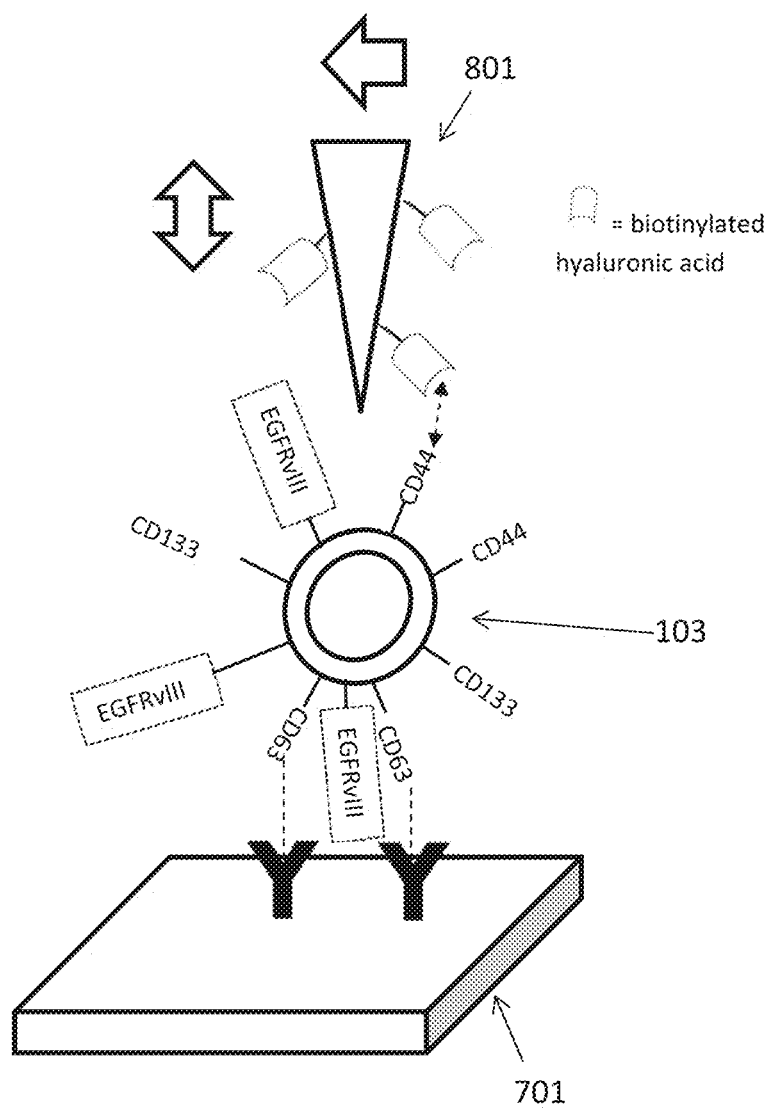
FIG. 12 illustrates a similar embodiment as that of FIG. 10, except that biotinylated hyaluronic acid is used instead of CD44AB.

In another embodiment, as illustrated in FIG. 12, the cantilever 801 tip is affixed with hyaluronic acid instead of CD44AB. It is possible to affix the hyaluronic acid to the cantilever 801 using biotin as the adhering element. Hyaluronic acid has an natural affinity to CD44 which allows for profiling of CD44 in the GBM exosomes.

In yet other embodiments, not illustrated, other ligands of CD44 can be affixed to the cantilever 801 instead of CD44AB or biotinylated hyaluronic acid, such as osteopontin, collagens, and matrix metalloproteinases (MMPs).

In a variation of the embodiments, CD133, CD133AB and other ligands for CD133 is used in place of CD44, CD44AB and other ligands for CD44, respectively. Alternatively, in other embodiments both CD133, CD133AB and other ligands for CD133 is used at the same time with CD44, CD44AB and other ligands for CD44. That is, the cantilever 801 of the Atomic Force Microscopy is affixed or doped with both CD133AB or CD44AB.

Although Localized Surface Plasmon Resonance and Atomic Force Microscopy has been described for characterizing exosomes by measuring the presence of cancer markers CD44, CD133 and/or EGFRviii, other analytic methods applied on the GBM exosomes are within contemplation of this application.

EXPERIMENT DATA

The following is a brief description of a piece of research made on in vivo detection and quantification of CD44 and CD133 in exosomes from blood and cerebrospinal fluid of an orthotopic mouse model of GBM. The results confirms the feasibility of the described novel use of exosomes from bodily fluids to monitor the prognosis of GBM.

To test the detection feasibility of GBM-derived exosomal biomarkers in vivo via using Atomic Force Microscopy and Localized Surface Plasmon Resonance biosensors, small amount of isolated exosomes from lactate- or vehicle-treated GMs were first mixed with the blood serum from wild-type mice, and increased level of CD44 and CD133 in exosomes from the serum mixture was detected through Atomic Force Microscopy biosensing, as shown in FIG. 13A. These results supports the feasibility of in vivo detection of exosomal CD44 and CD133 in the blood.

To validate whether the enhanced levels of CD44 and CD133 in malignant GBM in vivo could be quantified by Localized Surface Plasmon Resonance biosensor using exosomes from the peripheral blood and the cerebrospinal fluid of a mouse model of GBM, wherein intracranial implantation of U87 luciferase (Luc)-GMs into the brain of immunodeficient mice were conducted. GBM formation was identified by the detection of bioluminescence of U87 Luc-GMs in the mouse model of GBM. After confirming GBM formation, exosomes were isolated from the blood and the cerebrospinal fluid of the mice. The results showed that significant, high level of EGFRviii was detected in exosomes from the blood and the cerebrospinal fluid of the GBM mice by TiN-NH-LSPR biosensor, although a relatively weak non-specific response from exosomes of control mice was also detected.

FIG. 13B showed representative bioluminescence (BLI) images of the intracranial GBM of the mouse implanted with U87 Luc-GMs. FIG. 13C, FIG. 13D, FIG. 13E showed the response of EGFRviii, CD44 and CD133 taken from blood serum exosomes. Consistently, the exosomes from the mouse with U87 Luc-GBM had a greater response than that of the mouse that was used in a sham-operation. FIG. 13F, FIG. 13G, FIG. 13H showed the response of EGFRviii, CD44 and CD133 taken from cerebrospinal fluid. These results indicate that the blood- and the cerebrospinal fluid-derived exosomes contained GMs-derived exosomes.

Just as an increase in the presence of EGFRviii, a high quantity of CD44 and CD133 in exosomes from the blood and the cerebrospinal fluid of the GBM mice were also detected by the biosensor, indicating that exosomal CD44 and CD133 could be indeed prognostic biomarkers for malignant GBM.

FIG. 13C, FIG. 13D, FIG. 13F, FIG. 13G, FIG. 14, FIG. 15, FIG. 16, FIG. 17, FIG. 18, FIG. 19 all showed the cases in which each biomarker was expressed, between the sham control and the GBM mice.

However, there are multiple sources of exosomes in the blood and cerebrospinal fluid, and CD44 and CD133 are also expressed in other cell types in the periphery. To exclude exosomes from other origins, FIG. 20 shows how GMs-derived exosomes in the blood serum and the cerebrospinal fluid was isolated by magnetic dynabeads immunocapture using EGFRviii AB. Indeed, significant number of GMs-derived exosomes was identified in the blood and the cerebrospinal fluid. Importantly, significant level of CD44 and CD133 in immunocaptured GMs-derived exosomes were detected and quantified by TiN-NH-LSPR biosensor.

FIG. 21 showed that the phase response of CD44 was greater in the GMs. FIG. 22 showed the CD133 response was greater in the GMs. FIG. 23 showed the CD44 response was greater in phase response for the GBM mouse than that of the sham operated mouse. FIG. 24 showed the CD133 response was greater in phase response for the GBM mouse than that of the sham operated mouse. FIG. 25 shows the CD44 response was greater in total response for the GBM mouse than that of the sham operated mouse. FIG. 26 showed the CD133 response was greater in total response for the GBM mouse than that of the sham operated mouse.

These results further support the feasibility of exosomal CD44- and CD133-based liquid biopsy for determining GBM malignancy using sensitive Localized Surface Plasmon Resonance biosensor.

Abbreviations

GBM=glioblastoma
GMs=glioblastoma cells
EC=endothelial cells
TME=tumor microenvironment
HA=hyaluronic acid
ECM=extracellular matrix
CD 44=Cluster of Differentiation 44
CD 133=Cluster of Differentiation 133
EGFRviii=epidermal growth factor variant III
BBB=blood brain barrier
BCSFB=blood-cerebrospinal fluid barrier
SPR=surface plasmon resonance
LSPR=localized surface plasmon resonance
AFM=Atomic Force Microscopy
AB=antibodies
SCF=cerebrospinal fluid While there has been described in the foregoing description preferred embodiments of the present invention, it will be understood by those skilled in the technology concerned that many variations or modifications in details of design, construction or operation may be made without departing from the scope of the present invention as claimed.

What is claimed is:

1. A method of identifying and treating a subject having glioblastoma comprising:
(a) identifying the subject by,
(i) obtaining a sample of blood or cerebrospinal fluid-derived extracellular vesicles (EVs) from the subject;
(ii) mixing the sample with a plurality of streptavidin-coated magnetic beads so as to separate Epidermal Growth Factor Receptor Variant-III (EGFRviii)-containing EVs from the sample, wherein, each streptavidin-coated magnetic bead is further linked with biotin, which is in turn bound to an anti-EGFRviii antibody;
separating the EGFRviii-containing EVs from the sample by,
(ii-1) using a magnet to move the streptavidin-coated magnetic beads bound EGFRviii-containing EVs away from the sample;
(ii-2) using a release buffer solution to break the bonding between the EGFRviii-containing EVs and the anti-EGFRviii antibody on the streptavidin-coated magnetic beads; and
(ii-3) using the magnet to remove the streptavidin-coated magnetic beads from the EGFRviii-containing EVs,
(iii) affixing the separated EGFRviii-containing EVs on a titanium nitride substrate having a layer of biotinylated Cluster of Differentiation (CD) 63 antibody coated thereon, in which the separated EGFRviii-containing EVs are affixed on the titanium nitride substrate via the attraction between CD63 of the separated EGFRviii-containing EVs and the biotinylated CD63 antibody; and (iv) characterizing the expression of CD44 and CD133 on the separated EGFRviii-containing EVs via surface plasmonic resonance or atomic force microscopy; and (b) administering a treatment to the subject when the expression of CD44 and CD133 are found on the separated EGFRviii-containing EVs in step (a), wherein the treatment is selected from the group consisting of chemotherapy, radiation, surgery, and a combination thereof.

* * * * *